United States Patent
Cambos et al.

(10) Patent No.: US 12,364,653 B2
(45) Date of Patent: *Jul. 22, 2025

(54) METHOD FOR IMPROVING THE SENSORIAL PROPERTIES OF OIL-IN-WATER EMULSIONS

(71) Applicants: SOCIETE D'EXPLOITATION DE PRODUITS POUR LES INDUSTRIES CHIMIQUES SEPPIC, Paris (FR); TOTAL MARKETING SERVICES, Puteaux (FR)

(72) Inventors: Sophie Cambos, Castres (FR); Florence Clemenceau, Castres (FR); Emmanuelle Merat, Lautrec (FR); Cécile Taillebois, Salies (FR); Sabrina Mizael, Puteaux (FR); Corinne Stoltz, Thiais (FR); Nelly Michel, Maisons (FR); Benjamin Swoboda, Oregeval (FR)

(73) Assignees: SOCIETE D'EXPLOITATION DE PRODUITS POUR LES INDUSTRIES CHIMIQUES SEPPIC, Paris (FR); TOTALENERGIES ONETECH, Courbevoie (FR)

( * ) Notice: Subject to any disclaimer, the term of this patent is extended or adjusted under 35 U.S.C. 154(b) by 50 days.

This patent is subject to a terminal disclaimer.

(21) Appl. No.: 17/455,757

(22) Filed: Nov. 19, 2021

(65) Prior Publication Data

US 2022/0071861 A1    Mar. 10, 2022

Related U.S. Application Data

(62) Division of application No. 16/470,395, filed as application No. PCT/FR2017/053508 on Dec. 12, 2017, now abandoned.

(30) Foreign Application Priority Data

Dec. 16, 2016 (FR) ...................... 1662650

(51) Int. Cl.
| | | |
|---|---|---|
| A61K 8/06 | (2006.01) |
| A61K 8/29 | (2006.01) |
| A61K 8/31 | (2006.01) |
| A61K 8/35 | (2006.01) |
| A61K 8/41 | (2006.01) |
| A61K 8/49 | (2006.01) |
| A61Q 17/04 | (2006.01) |

(52) U.S. Cl.
CPC ............. *A61K 8/062* (2013.01); *A61K 8/29* (2013.01); *A61K 8/31* (2013.01); *A61K 8/35* (2013.01); *A61K 8/415* (2013.01); *A61K 8/4946* (2013.01); *A61K 8/4966* (2013.01); *A61Q 17/04* (2013.01)

(58) Field of Classification Search
CPC . A61K 8/062; A61K 8/29; A61K 8/31; A61K 8/35; A61K 8/415; A61K 8/4946; A61K 8/4966; A61Q 17/04
See application file for complete search history.

(56) References Cited

U.S. PATENT DOCUMENTS

| | | | |
|---|---|---|---|
| 6,013,270 A * | 1/2000 | Hargraves ........... B05B 11/1001 514/937 |
| 2005/0175572 A1 | 8/2005 | Nguyen-Kim et al. |
| 2006/0167117 A1 | 7/2006 | Leaym et al. |
| 2008/0161418 A1 | 7/2008 | Dierker |
| 2008/0262103 A1* | 10/2008 | Stork .................. A61K 8/345 514/772.6 |
| 2010/0135918 A1 | 6/2010 | Kim et al. |
| 2010/0183536 A1 | 7/2010 | Ansmann et al. |
| 2012/0171266 A1* | 7/2012 | Cantwell ............. A61K 8/8152 424/59 |
| 2013/0150322 A1 | 6/2013 | Paufique |
| 2015/0125403 A1 | 5/2015 | Joerger et al. |

FOREIGN PATENT DOCUMENTS

| | | |
|---|---|---|
| EP | 2 644 188 A1 | 10/2013 |
| JP | 2006-524200 A | 10/2006 |
| JP | 2010-530389 A | 9/2010 |
| JP | 2011/065771 A2 | 6/2011 |
| WO | 2004/084844 A2 | 10/2004 |
| WO | 2008/155060 A2 | 12/2008 |

OTHER PUBLICATIONS

Office Action issued in Japanese Patent Application No. 2019-531316 dated Oct. 12, 2021.
International Search Report, issued in International Application No. PCT/FR2017/053508, dated Dec. Feb. 16, 2018.

(Continued)

*Primary Examiner* — Robert A Wax
*Assistant Examiner* — Olga V. Tcherkasskaya
(74) *Attorney, Agent, or Firm* — NIXON & VANDERHYE

(57) ABSTRACT

Disclosed is a method for improving the sensorial and/or aesthetic properties of an oil-in-water type emulsion for topical application, the method including an effective quantity of a mixture of saturated cyclic or acyclic, linear or branched hydrocarbons of which at least 95% by weight have between fifteen and nineteen carbon atoms.

10 Claims, No Drawings

(56) References Cited

OTHER PUBLICATIONS

Agrana/AAK Sweden AB: "Winter Comfort Eco-conscious Hand Cream MAI SITA 9040", www.agrana.com Oct. 24, 2016 (Oct. 24, 2016), XP002770404,Retrieved from the Internet:URL:http://www.agrana.com/de/downloadcenter/?layout=thumbs&id=3739&no_cache=1&itemsPerPage=36 [retrieved on May 16, 20176] the whole document.

Jennifer Novoseletsky: "Seppic introduces Emollient Ranges by the Double", www.cosmeticsandtoiletries.com Apr. 17, 2016 (Apr. 17, 2016). XP002770405,Retrieved from the Internet:URL:http://www.cosmeticsandtoiletries.com/formulating/category/skincare/Seppic-Introduces-Emoll ient-Ranges-by-the-Double-375459721. html [retrieved on May 16, 2017] the whole document.

French Search Report, issued in French Application No. FR1662650 dated May 24, 2017.

\* cited by examiner

METHOD FOR IMPROVING THE SENSORIAL PROPERTIES OF OIL-IN-WATER EMULSIONS

CROSS-REFERENCE TO RELATED APPLICATIONS

This application is a divisional of application Ser. No. 16/470,395, filed Jun. 17, 2019, and claims priority to PCT/FR2017/053508 filed Dec. 12, 2017, which claims priority to French Application No. 1662650 filed Dec. 16, 2016.

BACKGROUND OF THE INVENTION

Field of the Invention

The subject of the invention is a novel method for improving the sensory and esthetic properties of an oil-in-water type emulsion on human skin.

Description of the Related Art

The objective of a large number of cosmetic formulations for topical application is to protect the skin, the mucous membranes and the scalp against external and environmental attacks and stresses. For example, consumers are looking for formulations to be applied to the skin that will protect them against the harmful and unesthetic effects of prolonged exposure to ultraviolet radiation from the sun, or that will protect against harmful modifications to the integrity of their skin following increasingly frequent exposure to the polluting agents present in atmospheres, and more particularly urban atmospheres.

To meet these demands aimed at maintaining and/or restoring skin integrity in the face of identified external elements or natural aging, the cosmetics and dermocosmetics industries have over the past few decades developed new specific ingredients for improving the performance levels required by consumers.

Furthermore, consumers are also waiting for properties of sensory and esthetic types provided by cosmetic and dermocosmetic compositions, which give them both feelings of well-being during and after application to the skin, and also an identification with an external appearance of the cosmetic or dermocosmetic formulation, which refers back to a criterion of quality. Thus, consumers are in search of cosmetic or dermocosmetic compositions, the high consistency of which, known as "richness", is often associated with a feeling of skin comfort during and after application to the skin. This feeling of comfort is reinforced when the step of spreading the cosmetic or dermocosmetic composition is easy, that is to say when its duration is reduced or more specifically is not prolonged as a consequence of resistance on the skin during said spreading and/or when the consumer must apply a high shear force on the skin, also resulting in a higher speed application on spreading and/or in the exerting of a force of higher intensity during said spreading phase.

In specific cases, for instance those of cosmetic or dermocosmetic formulations intended for prevention against the adverse effects (redness, erythema and burns) of ultraviolet radiation from the sun on the skin or those of creams intended for anti-inflammatory and antirheumatic treatments by local application, comprising for example ibuprofen, camphor, diclofenac or clove oil, which are characterized by difficulties in using them during spreading, it has been observed that consumers are less rigorous in the implementation of the procedures for application of said protection or care products. They thus often apply too little product and/or at a frequency that is not sufficiently maintained, and this then results in less protection of the skin than that provided for in the information sheet and/or on the packaging.

Thus, in order to encourage better and more frequent application of these prevention and protection formulations for the skin, it is important for said formulations to have pleasant sensory properties and for it to be possible to spread them on the skin uniformly and rapidly, without involving too great an application intensity.

Furthermore, consumers seek cosmetic or dermocosmetic formulations which do not detrimentally modify the external appearance of the skin, for instance by leaving an oily residue in the form of a slight film and, on the contrary, a cosmetic or dermocosmetic formulation which gives the skin a matt appearance will be preferred and sought.

Finally, the external appearance of the cosmetic or dermocosmetic formulation may constitute a criterion of choice and of proven attraction for its use by the consumer. Thus, a cosmetic or dermocosmetic formulation having a heterogeneous external appearance, showing a slight layer of yellowish oil at the surface after storage will not be considered to be attractive, whereas, on the contrary, a cosmetic or dermocosmetic formulation that is homogeneous after prolonged storage and that has a shiny appearance will be considered to be attractive since it reflects an external image of quality.

Taking all these requirements into consideration, those skilled in the art can only note that a large number of protection and care products, for instance antisun products or products for topical treatment of inflammations, which show great efficacy, nevertheless cause greasy and unpleasant sensations when they are spread on the skin, said spreading having to be carried out in a relatively long period of time requiring a greater application speed.

These protection and care formulations may be in the form of an oil-in-water type emulsion in order to be able to provide a more pleasant sensation by bringing the skin into contact with an aqueous phase, but the surfactant or polymeric emulsifiers required to maintain the stability of said oil-in-water emulsion may also contribute to discomfort during the application by conferring a sensation of heaviness on the emulsion during and after its application to the skin.

One alternative may consist of the development of a water-in-oil type emulsion, which is stabilized by thickening of the oily phase using in particular waxes and linear fatty alcohols, the hydrocarbon-based chain of which comprises from 14 to 22 carbon atoms. Silicone elastomers are also used to stabilize such a water-in-oil type emulsion, but said silicone elastomers also involve a deterioration of the sensory properties of the skin thus treated by the application of said emulsion. Moreover, the use of these silicone elastomers as stabilizers of water-in-oil antisun emulsions modifies, in some cases, the solubility of the sunscreens used, which can then precipitate from the bottle during storage.

In order to avoid being confronted with the drawbacks mentioned above both for water-in-oil type emulsions and for oil-in-water type emulsions, the formulator must develop an emulsion which has improved spreading properties, therefore making it possible for the consumer to apply the emulsion to the skin without being confronted with friction forces contrary to the movement set up by the applicator and therefore slowing down said application and/or requiring a higher spreading speed.

European patent application published under number EP 2 644 188 A1 teaches oil-in-water type emulsions having improved properties of spreading on the skin, comprising a combination of at least one crosslinked and non-emulsifying silicone resin, at least one polyvinyl alcohol, a thickener of polyacrylamide type, an oil chosen from the elements of the group consisting of triglyceride-type plant oils, waxes, ethoxylated fatty alcohols, fatty acid esters, fatty acids, fatty alcohols, silicone oils and perfluoro oils.

The international application published under number WO 2011/065771 discloses and teaches the spreading and the softness provided during the application of a water-in-oil-in-water type emulsion, prepared from a water-in-oil type emulsion comprising a silicone-based emulsifier, a di-polyhydroxalkyl type emulsifier, a mineral thickener of hectorite type, and a polar oil.

These prior art solutions describe an improvement in the spreading properties of an emulsion by using silicone compounds and other surfactants for which those skilled in the art seek an alternative in an approach where sustainable development is taken into account, and more particularly in an approach where use is made of ingredients that do not emit, and/or the production of which does not involve, volatile organic compounds (VOCs) and/or where use is made of biodegradable ingredients according to the regulatory standards in force and/or where use is made of ingredients of plant and no longer fossil origin. Some of the esthetic properties sought, for instance those aimed at giving the skin a matte appearance, are achieved by using, in the cosmetic formulation, polymers considered to be plastics and thus which an alternative to obtaining a matte effect on the skin is sought.

More specifically, silicone derivatives, such as the chemical substances and compositions of the polysiloxane family are known to give oil-in-water emulsions improved sensory properties, in particular in terms of ease of spreading and of limitation of lipid residues on the skin after application. However, the environmental characteristics associated with these ingredients have required the search for substitutes which provide similar sensory properties while at the same time having environmental characteristics in accordance with the regulations in force and to come, and in accordance with consumer demands on the subject. A partially satisfactory alternative has been demonstrated, by the use of alkane compositions comprising large amounts of cycloalkanes for preparing oil-in-water cosmetic emulsions; said alkane mixtures having biodegradability properties that are satisfactory and sensory properties that are satisfactory but judged to have room for improvement.

Consequently, there is a need to develop cosmetic or dermocosmetic formulations which have improved sensory properties, in particular which provide a sensation of richness and which are easy to spread on the skin, and which have improved and/or attractive esthetic characteristics, for instance which are characterized by an improved shiny appearance and which give the skin a matte and non-shiny appearance.

SUMMARY OF THE INVENTION

The inventors have thus sought to develop a new solution for improving the sensory and esthetic properties of an oil-in-water type emulsion for topical use, not necessarily using silicone derivatives, but using chemical compositions of plant and/or biodegradable origins.

Consequently, according to a first aspect, a subject of the invention is a method for improving the sensory and/or esthetic properties of an oil-in-water type emulsion ($E_0$), said sensory properties being the spreading properties and the consistency and richness properties of said topical emulsion ($E_0$), characterized in that an effective amount of a mixture ($M_1$) of cyclic or acyclic, linear or branched saturated hydrocarbons, among which at least 95% by weight comprise 15 to 19 carbon atoms, is incorporated into said oil-in-water type emulsion ($E_0$). According to one particular aspect, said oil-in-water type emulsion ($E_0$) is free of shea butter.

For the purposes of the present invention, the term "sensory properties" of an oil-in-water ($E_0$) denotes the sensations felt and noted by a user who applies to the skin the oil-in-water type emulsion (E) resulting from said method above and which correspond to physicochemical and/or rheological characteristics of said emulsion (E).

For the purposes of the present invention, the term "esthetic properties" denotes visual characteristics associated with the oil-in-water emulsion for use (E) as such and also 10 associated with the condition of the skin after application of said oil-in-water emulsion for topical use (E).

The term "effective amount" denotes, in the definition of the method as defined above, an amount such that the oil-in-water type emulsion for topical use (E) resulting from said method above: shows a mean value of at least three measurements of the variation in the coefficient of friction, as a function of the velocity of application of between 1 radian·s$^{-1}$ and 4 radian·s$^{-1}$, of less than or equal to 10% of the value initially measured for a velocity of application to the skin equal to 1 radian·s$^{-1}$; said coefficients of friction being recorded during each of the measurements by means of a DHR2 rheometer (TA Instruments) equipped with a support of Peltier plate type on which is placed a plexiglass surface on which the emulsion to be tested is deposited.

For the purposes of the present invention, the term "oil-in-water type emulsion ($E_0$)" denotes the emulsions comprising, for 100% of their weight:
  from 95% to 50%, more particularly from 90% to 70% of a cosmetically acceptable aqueous phase ($A_0$);
  from 5% to 50%, more particularly from 10% to 30% of a fatty phase ($G_0$), said fatty phase ($G_0$) comprising, for 100% of its weight, from 1% to 12%, more particularly from 2% to 8% of at least one oil-in-water type surfactant and from 88% to 99%, more particularly from 92% to 98% of at least one oil and/or one wax.

For the purposes of the invention, the term "oil" present in the fatty phase ($G_0$) of the oil-in-water type emulsion ($E_0$) as defined above denotes chemical substances or mixtures of chemical substances that are water-insoluble and that are in liquid form at a temperature of 25° C.

For the purposes of the invention, the term "wax" present in the fatty phase ($G_0$) of the oil-in-water type emulsion ($E_0$) as defined above denotes the chemical substances or the mixtures of chemical substances that are water-insoluble and that are in solid form at a temperature of 45° C.

For the purposes of the present invention, the term "water-in-oil type surfactant" present in the fatty phase ($G_0$) of the oil-in-water type topical emulsion ($E_0$) as defined above denotes the chemical substance of the mixture of chemical substances that makes it possible to stabilize the droplets of said fatty phase ($G_0$) in dispersion in the continuous phase ($A_0$).

As oil-in-water type surfactant present in the fatty phase ($G^0$) of the oil-in-water type emulsion ($E_0$) as defined above, mention may be made for example of:
  polysorbates resulting from the ethoxylation reaction of one molar equivalent of sorbitan esters and between 5 and 20 molar equivalents of ethylene oxide, and more particularly between one molar equivalent of sorbitan laurate, of sorbitan palmitate, or of sorbitan stearate, or of sorbitan isostearate, or of sorbitan oleate, and between 5 and 20 molar equivalents of ethylene oxide;

the products resulting from the ethoxylation reaction between one molar equivalent of a fatty acid, for instance palmitic acid, myristic acid, lauric acid, stearic acid, isostearic acid, oleic acid, and between 5 and 40 molar equivalents of ethylene oxide;

the products resulting from the esterification reaction between a fatty acid, for instance palmitic acid, myristic acid, lauric acid, stearic acid, isostearic acid, oleic acid, arachidic acid, behenic acid, and between 4 and 20 molar equivalents, more particularly between 3 and 10 molar equivalents, of glycerol.

The expression "cosmetically acceptable" used in the definition of the aqueous phase ($A_O$) of the oil-in-water type emulsion means, according to the Council of the European Economic Community Directive no. 76/768/EEC of Jul. 27, 1976, amended by Directive no. 93/35/EEC of Jun. 14, 1993, any substance or preparation intended to be brought into contact with the various parts of the human body (epidermis, body hair and head hair system, nails, lips and genitals) or with the teeth and mucous membranes of the mouth, for the purpose, exclusively and mainly, of cleansing them, fragrancing them, modifying the appearance thereof and/or correcting body odors thereof and/or protecting them or keeping them in good condition. A cosmetically acceptable medium of these compositions which are a subject of the invention may conventionally contain water, one or more cosmetically acceptable organic solvents, or a mixture of water and one or more organic solvents. The cosmetically acceptable solvents may more particularly be chosen from polyhydric alcohols, for instance glycerol, diglycerol, glycerol oligomers, ethylene glycol, propylene glycol, hexylene glycol, diethylene glycol, xylitol, erythritol, sorbitol, or water-soluble alcohols.

According to one particular mode of the method as defined above, the term "effective amount of said mixture ($M_1$)" denotes a weight proportion of from 1% to 25% of the oil-in-water emulsion, most particularly from 5% to 20%.

The expression "for topical use" used in the definition of the method as defined above means that said composition is used by application to the skin, the hair, the scalp or the mucous membranes, whether it is a direct application in the case of a cosmetic, dermocosmetic, dermopharmaceutical or pharmaceutical composition or an indirect application, for example in the case of a body hygiene product in the form of a textile or paper wipe, or sanitary products intended to be in contact with the skin or the mucous membranes.

For the purposes of the present invention, the term "linear alkanes" present in the mixture ($M_1$) used in the method which is a subject of the present invention, and comprising from fifteen to nineteen carbon atoms, denotes more particularly the elements chosen from the group consisting of pentadecane, hexadecane, heptadacane, octadecane and nonadecane.

For the purposes of the present invention, the term "branched alkanes" present in the mixture ($M_1$) used in the method which is a subject of the present invention, and comprising from fifteen to nineteen carbon atoms, denotes more particularly the elements chosen from the group consisting of 2-methyltetradecane (or isopentadecane), 2-methylpentadecane (or isohexadecane), 2-methylhexadecane (or isoheptadecane), 2-methylheptadecane (or isooctadecane) and 2-methyloctadecane (or isononadecane).

For the purposes of the present invention, the term "cycloalkanes" present in the mixture ($M_1$) used in the method which is a subject of the present invention, and comprising from 15 to 19 carbon atoms, denotes more particularly saturated hydrocarbons comprising at least one saturated cyclic hydrocarbon-based group optionally substituted with one or more linear or branched alkyl radicals.

According to one particular aspect, a subject of the invention is a method as defined above, characterized in that said mixture ($M_1$) comprises, for 100% of its weight:
  a weight proportion of branched alkanes of greater than or equal to 80% and less than or equal to 100%, and more particularly greater than or equal to 90%;
  a weight proportion of linear alkanes of greater than or equal to 0% and less than or equal to 15%, and more particularly less than or equal to 10%;
  a weight proportion of cycloalkanes of greater than or equal to 0% and less than or equal to 5%, and more particularly less than or equal to 1%, and in that from 95% by weight to 100% by weight of said cyclic or acyclic, linear or branched hydrocarbons comprise from fifteen to nineteen carbon atoms and in that up to 5% by weight of said cyclic, acyclic, linear or branched hydrocarbons comprise less than fifteen carbon atoms or more than nineteen carbon atoms.

According to a more particular aspect, the subject of the invention is a method as defined above, wherein ($M_1$) is a mixture of saturated hydrocarbons sold under the brand name Emogreen™ML15, comprising, for 100% of its weight:
  i) 3.7% of linear alkanes comprising from fifteen to nineteen carbon atoms,
  ii) 96% of isoalkanes comprising from fifteen to nineteen carbon atoms, and
  iii) 0.3% of cycloalkanes comprising from fifteen to nineteen carbon atoms.

According to another more particular aspect, a subject of the invention is a method as defined above, characterized in that said mixture ($M_1$) comprises, for 100% of its weight:
  a weight proportion of branched alkanes of greater than or equal to 40% and less than or equal to 100%, and more particularly greater than or equal to 50% by weight,
  a weight proportion of linear alkanes of greater than or equal to 0% and less than or equal to 20%, and more particularly less than or equal to 15% by weight,
  a weight proportion of cycloalkanes of greater than or equal to 0% and less than or equal to 40%, and more particularly less than or equal to 35% by weight, and in that 100% by weight of said cyclic or acyclic, linear or branched hydrocarbons comprise from fifteen to nineteen carbon atoms.

According to a most particular aspect, the subject of the invention is a method as defined above, wherein ($M_1$) is a mixture of saturated hydrocarbons sold under the brand name Emosmart™L19, comprising, for 100% of its weight:
  i) 13.20% by weight of linear alkanes comprising from 15 to 19 carbon atoms,
  ii) 55.00% by weight of isoalkanes comprising from 15 to 19 carbon atoms, and
  iii) 31.80% of cycloalkanes comprising from 15 to 19 carbon atoms.

For the purposes of the present invention, the term "properties of spreading on the skin" denotes the capacity for the oil-in-water emulsion that is the subject of the present invention to be spread on the surface of the skin in a thin layer and so as to cover a wide surface area of the skin while at the same time remaining sufficiently concentrated to accomplish its assigned mission by virtue of its composition, for instance the protection of the skin against the consequences of prolonged exposure to ultraviolet radiation from sun if the oil-in-water emulsion contains organic and/or inorganic sunscreens. The properties of spreading on the skin of an oil-in-of water type emulsion, namely the ease or difficulty in spreading said emulsion on human skin, can be evaluated by implementing various methods, for instance methods which make it possible to measure the yield point values and/or to measure the shear-thinning index, and/or to measure the coefficient of friction, and/or to measure the variation in the coefficient of friction as a function of the rapidity of said spreading.

For the purposes of the present invention, the term "richness" of said emulsion for topical use ($E_0$) denotes the sensation provided by the application to the skin of an emulsion for topical use ($E_0$), as defined above, which is characterized by a non-fluid or non-runny compact consistency if subjected solely to the force of gravity, and a presence of the emulsion during spreading on the skin that is significantly greater in comparison with the spreading of water; the term "presence" is thus understood by those skilled in the art to be a sensory perception devoid of an aqueous nature.

According to another particular aspect, a subject of the invention is the method as defined above, for which the esthetic property is the shininess of the oil-in-water type emulsion for topical use ($E_0$) resulting from said method above. For the purpose of the present invention, the term "shininess" denotes the capacity of the emulsion to reflect incident rays originating from a source of light of the visible spectrum with a given reflection yield.

According to another particular aspect, a subject of the invention is the method as defined above, for which the esthetic property is the mattt appearance of the skin noted after the application to the skin of an oil-in-water type emulsion for topical use ($E_0$) resulting from said method above. For the purposes of the present invention, the term "matt aspect of the skin" denotes the capacity of the skin to absorb a given proportion of incident rays originating from a source of light of the visible spectrum, said capacity being linked to the thickness and the nature of the residual film of emulsion remaining on the skin after application thereof.

A subject of the invention is also an oil-in-water type emulsion (E) comprising, for 100% of its weight:
  from 50% to 90% by weight, more particularly from 60% to 90% by weight and even more particularly from 70% to 90% by weight of a cosmetically acceptable aqueous phase (A);
  from 10% to 50% by weight, more particularly from 10% to 40% by weight and even more particularly from 10% to 30% by weight of a fatty phase (G) comprising, for 100% of its weight:
  from 10% to 50% by weight, more particularly from 15% to 40% by weight of a mixture ($M_1$) of saturated cyclic or acyclic, linear or branched hydrocarbons among which at least 95% by weight comprise from fifteen to nineteen carbon atoms;
  from 0.5% to 15% by weight, more particularly from 1% to 10% by weight of at least one oil-in-water type surfactant;
  from 5% to 30% by weight, more particularly from 15% to 30% by weight of at least one agent for protection against ultraviolet rays from the sun;
  from 0% to 80% by weight, more particularly from 0% to 60% by weight of at least one oil and/or one wax, it being understood that such an oil and/or such a wax do not correspond to the definition of the mixture ($M_1$).

According to one particular aspect, said oil-in-water type emulsion (E) is free of shea butter.

For the purposes of the present invention, the term "fatty phase (G)" denotes a fatty substance or a mixture of fatty substances that is insoluble in water and/or in mixtures of water and polar solvents. Such a "fatty phase" may comprise oils and/or waxes. Among the constituent elements of the fatty phase, mention may be made of:
  oils of animal origin, such as squalene or squalane;
  plant oils, such as phytosqualane, sweet almond oil, coconut oil, castor oil, jojoba oil, olive oil, rapeseed oil, groundnut oil, sunflower oil, wheat germ oil, corn germ oil, soybean oil, cottonseed oil, alfalfa oil, poppy oil, pumpkin oil, evening primrose oil, millet oil, barley oil, rye oil, safflower oil, candlenut oil, passionflower oil, hazelnut oil, palm oil, apricot kernel oil, beauty leaf oil, sysymbrium oil, avocado oil, calendula oil, sesame oil, meadowsweet oil, macadamia/kiwi oil, borage oil, blackcurrant oil, coffee oil, pistachio oil, peach kernel oil, rapberry seed oil, strawberry seed oil, melon oil, blueberry seed oil, argan oil, oily plum extract, pomegranate oil, *papaya* oil, coconut milk oil, and oils derived from flowers or from vegetables;
  ethoxylated plant oils;
  synthetic oils for instance fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate, isocetyl lanolate, fatty acid monoglycerides, diglycerides and triglycerides, such as glyceryl triheptanoate, alkyl benzoates, hydrogenated oils, poly(alpha-olefins), polyolefins such as polyisobutene, hydrogenated polydecene or hydrogenated polyisobutene, sold in France by the company Ets B. Rossow et Cie under the name Parleam-Polysynlane™, cited in: Michel and Irene Ash; Thesaurus of Chemical Products, Chemical Publishing Co, Inc. 1986 Volume I, page 211 (ISBN 0 7131 3603 0);
  silicone oils such as dimethylpolysiloxanes, methylphenylpolysiloxanes, amine-modified silicones, fatty acid-modified silicones, alcohol-modified silicones, silicones modified with alcohols and fatty acids, silicones modified with polyether groups, epoxy-modified silicones, silicones modified with fluoro groups, cyclic silicones and silicones modified with alkyl groups.
  waxes such as beeswax, carnauba wax, candelilla wax, ouricoury wax, Japan wax, cork fiber wax, sugar cane wax, jojoba wax, blackcurrant flower wax, *narcissus* flower wax, orange tree flower wax, orange wax, rice wax, paraffin waxes, lignite waxes, microcrystalline waxes, lanolin wax; ozokerite; polyethylene wax; silicone waxes; plant waxes; fatty alcohols and fatty acids that are solid at ambient temperature; glycerides that are solid at ambient temperature.

The term "water-in-oil type surfactant" present in the fatty phase (G) of the oil-in-water type emulsion (E) as defined above denotes a chemical substance or the mixture of chemical substances that makes it possible to stabilize the droplets of the fatty phase (G) in dispersion in the continuous phase (A). Mention may for example be made of:
  polysorbates resulting from the ethoxylation reaction of one molar equivalent of sorbitan esters and between 5 and 20 molar equivalents of ethylene oxide, and more particularly between one molar equivalent of sorbitan laurate, of sorbitan palmitate, or of sorbitan stearate, or of sorbitan isostearate, or of sorbitan oleate, and between 5 and 20 molar equivalents of ethylene oxide;

the products resulting from the ethoxylation reaction between one molar equivalent of a fatty acid, for instance palmitic acid, myristic acid, lauric acid, stearic acid, isostearic acid, oleic acid, and between 5 and 40 molar equivalents of ethylene oxide;

the products resulting from the esterification reaction between a fatty acid, for instance palmitic acid, myristic acid, lauric acid, stearic acid, isostearic acid, oleic acid, arachidic acid, behenic acid, and between 4 and 20 molar equivalents, more particularly between 3 and 10 molar equivalents, of glycerol.

A cosmetically acceptable aqueous phase (A) included in the oil-in-water emulsion (E) as defined above may conventionally contain one or more cosmetically acceptable organic solvents, or a mixture of water and one or more cosmetically acceptable organic solvents. The cosmetically acceptable solvents may more particularly be chosen from polyhydric alcohols, for instance glycerol, diglycerol, triglycerol, glycerol oligomers, xylitol, erythritol, sorbitol, 2-methyl-1,3-propanediol; alkoxylated polyhydric alcohols; glycols, for instance butylene glycol, hexylene glycol, caprylyl glycol or 1,2-octanediol, pentylene glycol or 1,2-pentanediol, monopropylene glycol, dipropylene glycol, isoprene glycol, butyldiglycol, polyethylene glycols, the molecular weight of which is between 200 $g \cdot mol^{-1}$ and 8000 $g \cdot mol^{-1}$; or water-soluble alcohols, for instance ethanol, isopropanol or butanol.

The term "agent for protecting against ultraviolet radiation from the sun" denotes in particular, in the definition of the oil-in-water type emulsion (E) which is a subject of the present patent application, pigments, organic sunscreens and inorganic sunscreens.

As pigments used as an agent for protecting against ultraviolet radiation from the sun, there are for example titanium dioxide, brown iron oxides, yellow iron oxides, black iron oxides or red iron oxides, or else white or colored nacreous pigments such as titanium mica.

As organic sunscreens used as an agent for protecting against ultraviolet radiation from the sun, there are for example:

those of the family of benzoic acid derivatives, such as para-aminobenzoic acids (PABAs), in particular monoglyceryl esters of PABA, ethyl esters of N,N-propoxy PABA, ethyl esters of N, N-diethoxy PABA, ethyl esters of N, N-dimethyl PABA, methyl esters of N, N-dimethyl PABA, butyl esters of N,N-dimethyl PABA;

those of the family of anthranilic acid derivatives, such as homomenthyl-N-acetyl anthranilate;

those of the family of salicylic acid derivatives, such as amyl salicylate, homomenthyl salicylate, ethylhexyl salicylate, phenyl salicylate, benzyl salicylate, p-isopropanolphenyl salicylate;

those of the family of cinnamaic acid derivatives, such as ethylhexyl cinnamate, ethyl-4-isopropyl cinnamate, methyl-2,5-diisopropyl cinnamate, p-methoxypropyl cinnamate, p-methoxyisopropyl cinnamate, p-methoxyisoamyl cinnamate, p-methoxyoctyl cinnamate (p-methoxy 2-ethylhexyl cinnamate), p-methoxy 2-ethoxyethyl cinnamate, p-methoxycyclohexyl cinnamate, ethyl-a-cyano-β-phenyl cinnamate, 2-ethylhexyl-Da-cyano-β-phenyl cinnamate, glyceryl diparamethoxy mono-2-ethylhexanoyl cinnamate;

those of the family of benzophenone derivatives, such as 2,4-dihydroxybenzophenone, 2,2'-dihydroxy-4-methoxybenzophenone, 2,2', 4,4'-tetrahydroxybenzophenone, 2-hydroxy-4-methoxybenzophenone, 2-hydroxy-4-methoxy-4'-methylbenzophenone, 2-hydroxy 4-methoxy benzophenone-5-sulfonate, 4-phenylbenzophenone, 2-ethylhexyl-4'-phenyl benzophenone-2-carboxylate, 2-hydroxy 4-n-octyloxybenzophenone, 4-hydroxy 3-carboxybenzophenone; 3-(4'-methylbenzylidene)-d, I-camphor, 3-(benzylidene)-d,I-camphor, benzalkonium methosulfate camphor; urocanic acid, ethyl urocanate;

those of the family of sulfonic acid derivatives, such as 2-phenylbenzimidazole-5-sulfonic acid and salts thereof; the family of triazine derivatives, such as hydroxyphenyltriazine, ethylhexyloxyhydroxyphenyl-4-methoxyphenyltriazine, benzoic acid 2,4,6-trianillino-(p-carbo-2'-ethylhexyl-1'-oxy)-1,3,5-triazine, 4,4-((6-(((1,1-dimethylethyl)amino) carbonyl)phenyl) amino)-1,3,5-triazine-2,4-diyldiimino)bis(2-ethylhexyl) ester, 2-phenyl-5-methylbenzoxazole, 2,2'-hydroxy-5-methylphenylbenzotriazole, 2-(2'-hydroxy-5'-t-octylphenyl)benzotriazole, 2-(2'-hydroxy-5'-methyphenyl)benzotriazole; dibenzazine; dianisoylmethane, 4-methoxy-4"-t-butylbenzoylmethane; 5-(3,3-dimethyl-2-norbornylidene)-3-pentan-2-one; 2-(4-diethylamino-2-hydroxybenzoyl)benzoic acid hexyl ester, 2,4-bis {[4-(2-ethylhexyloxy)-2-hydroxy]phenyl}-6-(4-methoxyphenyl)-1,3,5-triazine, 2,4,6-tris [4-(2-ethylhexyloxycarbonyl) anilino]-1,3,5-triazine, 2-ethylhexyl dimethoxybenzylidene dioxoimidazolidine propionate, the family of diphenylacrylate derivatives, such as 2-ethylhexyl-2-cyano-3,3-diphenyl-2-propenoate, ethyl-2-cyano-3,3-diphenyl-2-propenoate;

those of the family of polysiloxanes, such as benzylidene siloxane malonate.

As inorganic sunscreens used as an agent for protecting against ultraviolet radiation from the sun, there are for example: titanium oxides, zinc oxides, cerium oxide, zirconium oxide, yellow, red or black iron oxides, chromium oxides. These mineral screens may or may not be micronized, may or may not have undergone surface treatments and may be optionally provided in the form of aqueous or oily predispersions.

According to one particular aspect, a subject of the invention is an oil-in-water emulsion for topical use (E) as defined above, wherein the agent for protecting against ultraviolet radiation from the sun is chosen from the elements of the group consisting of titanium dioxide, 2,4-dihydroxybenzophenone, 2-(4-diethylamino-2-hydroxybenzoyl)benzoic acid hexyl ester, le 2,4-bis {[4-(2-ethylhexyloxy)-2-hydroxy]phenyl}-6-(4-methoxyphenyl)-1,3,5-triazine, 2,4,6-tris [4-(2-ethylhexyloxy carbonyl) anilino]-1,3,5-triazine and 2-ethylhexyl dimethoxybenzylidene dioxoimidazolidine propionate.

According to one particular aspect, a subject of the invention is an oil-in-water emulsion (E) as defined above, characterized in that said mixture ($M_1$) comprises, for 100% of its weight:

a weight proportion of branched alkanes of greater than or equal to 80% and less than or equal to 100%, and more particularly greater than or equal to 90% by weight, a weight proportion of linear alkanes of greater than or equal to 0% and less than or equal to 15%, and more particularly less than or equal to 10% by weight, a weight proportion of cycloalkanes of greater than or equal to 0% and less than or equal to 5%, and more particularly less than or equal to 1% by weight, in that from 95% by weight to 100% by weight of said cyclic or acyclic, linear or branched hydrocarbons comprise from fifteen to nineteen carbon atoms and in that up to 5% by weight of said cyclic, acyclic, linear or branched hydrocarbons comprise less than fifteen carbon atoms or more than nineteen carbon atoms.

According to this particular aspect, said mixture ($M_1$) is more particularly a mixture of saturated hydrocarbons sold under the brand name Emogreen™L15, comprising, for 100% of its weight:
  i) 3.7% of linear alkanes comprising from fifteen to ninteen carbon atoms,
  ii) 96% of isoalkanes comprising from fifteen to ninteen carbon atoms, and
  iii) 0.3% of cycloalkanes comprising from fifteen to ninteen carbon atoms.

According to another more particular aspect, the oil-in-water type emulsion (E) as defined above is characterized in that said mixture ($M_1$) comprises, for 100% of its weight:
  a weight proportion of branched alkanes of greater than or equal to 40% and less than or equal to 100%, and more particularly greater than or equal to 50% by weight,
  a weight proportion of linear alkanes of greater than or equal to 0% and less than or equal to 20%, and more particularly less than or equal to 15% by weight,
  a weight proportion of cycloalkanes of greater than or equal to 0% and less than or equal to 40%, and more particularly less than or equal to 35% by weight, and in that 100% by weight of said cyclic or acyclic, linear or branched hydrocarbons comprise from fifteen to nineteen carbon atoms.

According to this particular aspect, the mixture ($M_1$) is more particularly a mixture of saturated hydrocarbons sold under the brand name Emosmart™ML19, comprising, for 100% of its weight:
  i) 13.20% by weight of linear alkanes comprising from 15 to 19 carbon atoms,
  ii) 55.00% by weight of isoalkanes comprising from 15 to 19 carbon atoms, and
  iii) 31.80% of cycloalkanes comprising from 15 to 19 carbon atoms.

The emulsion (E) as defined above may comprise one or more adjuvants such as:
  thickeners or gelling agents, for example linear or branched or crosslinked polymers of polyelectrolyte type, such as the partially or totally salified acrylic acid homopolymer, the partially or totally salified methacrylic acid homopolymer, the partially or totally salified 2-methyl-[(1-oxo-2-propenyl)amino]-1-propanesulfonic acid (AMPS) homopolymer, copolymers of acrylic acid and of AMPS, copolymers of acrylamide and of AMPS, copolymers of vinylpyrrolidone and of AMPS, copolymers of AMPS and of (2-hydroxyethyl) acrylate, copolymers of AMPS and of (2-hydroxyethyl) methacrylate, copolymers of AMPS and of hydroxyethylacrylamide, copolymers of AMPS and of N, N-dimethylacrylamide, copolymers of AMPS and of tris (hydroxymethyl) acrylamidomethane (THAM), copolymers of acrylic or methacrylic acid and of (2-hydroxyethyl) acrylate, copolymers of acrylic or methacrylic acid and of (2-hydroxyethyl) methacrylate, copolymers of acrylic or methacrylic acid and of hydroxyethylacrylamide, copolymers of acrylic or methacrylic acid and of THAM, copolymers of acrylic or methacrylic acid and of N,N-dimethylacrylamide, terpolymers of acrylic or methacrylic acid, of AMPS and of (2-hydroxyethyl) acrylate, terpolymers of acrylic or methacrylic acid, of AMPS and of (2-hydroxyethyl) methacrylate, terpolymers of acrylic or methacrylic acid, of AMPS and of THAM, terpolymers of acrylic or methacrylic acid, of AMPS and of N,N-dimethylacrylamide, terpolymers of acrylic or methacrylic acid, of AMPS and of acrylamide, copolymers of acrylic acid or methacrylic acid and of alkyl acrylates, the carbon chain of which comprises between 4 and 30 carbon atoms and more particularly between 10 and 30 carbon atoms, copolymers of AMPS and of alkyl acrylates, the carbon chain of which comprises between 4 and 30 carbon atoms and more particularly between 10 and 30 carbon atoms, linear, branched or crosslinked terpolymers of at least one monomer having a free, partially salified or totally salified strong acid function, with at least one neutral monomer, and at least one monomer of formula (VIII):

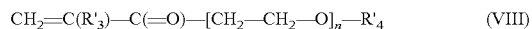

$$CH_2=C(R'_3)-C(=O)-[CH_2-CH_2-O]_n-R'_4 \qquad (VIII)$$

wherein R'3 represents a hydrogen atom or a methyl radical, R'4 represents a linear or branched alkyl radical comprising from eight to thirty carbon atoms and n represents a number greater than or equal to one and less than or equal to 50; the linear or branched or crosslinked polymers of polyelectrolyte type that can be combined with the oil-in-water emulsion that is a subject of the present invention may be in the form of a solution, of an aqueous suspension, of a water-in-oil emulsion, of an oil-in-water emulsion or of a powder, for example the products sold under the names Simulgel™ EG, Simulgel™MEPG, Sepigel™ 305, Simulgel™ 600, Simulgel™ NS, Simulgel™ INS 100, Simulgel™ FL, Simulgel™ A, Simulgel™ SMS 88, Sepinov™MEMT 10, Sepiplus™400, Sepiplus™ 265, Sepiplus™S, Sepimax™ Zen, Aristoflex™MAVC, Aristoflex™ AVS, NovemerTEC-1, Novemer™MEC 2, Aristoflex™HMB, Cosmedia™SP, Flocare™MET 25, Flocare™MET 75, Flocare™MET 26, Flocare™MET 30, Flocare™MET 58, Flocare™PSD 30, Viscolam™MAT 64, Viscolam™AT 100; polysaccharides consisting only of monosaccharides, such as glucans or glucose homopolymers, glucomannoglucans, xyloglycans, galactomannans of which the degree of substitution (DS) of the D-galactose units on the main chain of D-mannose is between 0 and 1, and more particularly between 1 and 0.25, such as galactomannans originating from *cassia* gum (DS=1/5), from locust bean gum (DS=1/4), from tara gum (DS=1/3), from guar gum (DS=1/2), from fenugreek gum (DS=1); polysaccharides consisting of monosaccharide derivatives, such as sulfated galactans and more particularly carrageenans and agar, uronans and more particularly algins, alginates and pectins, heteropolymers of monosaccharides and of uronic acids and more particularly xanthan gum, gellan gum, exudates of gum arabic and of karaya gum, glucosaminoglycans; cellulose, cellulose derivatives such as methylcellulose, ethylcellulose, hydroxypropylcellulose, silicates, starch, hydrophilic starch derivatives, polyurethanes;
  film-forming compounds;
  hydrotropic agents;
  plasticizers;
  opacifiers or nacreous agents, such as sodium or magnesium palmitate, stearate or hydroxystearate, ethylene or polyethylene glycol monostearates or distearate, fatty alcohols, styrene homopolymers and copolymers, such as the styrene acrylate copolymer sold under the name Montopol™ OP1 by the company SEPPIC;
  texturing agents, such as the lauroyl lysine sold under the name Aminohope™LL by the company Ajinomoto, the octenyl starch succinate sold under the name Dryflo™ by the company National Starch, the myristyl polyglucoside sold by SEPPIC under the name Montanov™ 14, cellulose fibers, cotton fibers, chitosan fibers, talc, sericite, mica;

overfatting agents;
sequestrants;
chelating agents;
nonionic surfactants such as ethoxylated derivatives of fatty alcohols comprising from 8 to 12 carbon atoms; ethoxylated derivatives of fatty acids comprising from 8 to 12 carbon atoms; ethoxylated derivatives of fatty esters comprising from 8 to 12 carbon atoms; ethoxylated derivatives of monoglycerides comprising from 8 to 12 carbon atoms; alkyl polyglycosides of formula (II):
wherein y represents a decimal number between 1 and 5, S represents the residue of a reducing sugar and $R_2$ represents a linear or branched, saturated or unsaturated alkyl radical having from 5 to 16 carbon atoms, preferably from 8 to 14 carbon atoms, or a mixture of compounds of formula (II), for example caprylyl capryl glucosides, sold in particular under the brand name Oramix™MCG 110, decylglucoside, sold in particular under the brand name Oramix™NS 10;
antioxidants, such as EDTA and salts thereof, citric acid, tartaric acid, oxalic acid, BHA (butylhydroxyanisole), BHT (butylhydroxytoluene), tocopherol derivatives such as tocopheryl acetate, mixtures of antioxidant compounds such as Dissolvine GL 47S (INCI name:
fragrances;
preservatives;
conditioning agents;
active ingredients intended to provide a treating action with respect to the skin or the hair, such as vitamins and derivatives thereof, especially esters thereof, such as retinol (vitamin A) and the esters thereof (retinyl palmitate, for example), ascorbic acid (vitamin C) and the esters thereof, sugar derivatives of ascorbic acid (such as ascorbyl glucoside), tocopherol (vitamin E) and the esters thereof (such as tocopheryl acetate), vitamin B3 or B10 (niacinamide and derivatives thereof); compounds showing a soothing action, especially Sepicalm™ S, allantoin and bisabolol; anti-inflammatoirempounds showing a moisturizing action, such as urea, hydroxyureas, glycerolglucoside, diglycerolglucoside, polyglycerylglucosides; polyphenol-rich plant extracts, such as grape extracts, pine extracts, wine extracts, olive extracts; compounds showing a slimming or lipolytic action, such as caffeine or derivatives thereof, Adiposlim™, Adipoless™, fucoxanthine; N-acylated proteins; N-acylated peptides, such as Matrixil™; N-acylated amino acids; partial hydrolysates of N-acylated proteins; amino acids; peptides; total protein hydrolysates; soybean extracts, for example Raffermine™; wheat extracts, for example Tensine™ or Gliadine™; plant extracts, such as tannin-rich plant extracts, isoflavone-rich plant extracts or terpene-rich plant extracts; extracts of freshwater or seawater algae; marine plant extracts; marine extracts in general, such as corals; essential waxes; bacterial extracts; ceramides; phospholipids; compounds showing an antimicrobial action or a purifying action, such as Lipacide™ C8G, Lipacide™ UG, Sepicontrol™ A5; Octopirox™ or Sensiva™ SC50; compounds showing an energizing or stimulating property, such as Physiogenyl™, panthenol and derivatives thereof, such as Sepicap™ MP; anti-aging active agents, such as Sepilift™ DPHP, Lipacide™ PVB, Sepivinol™, Sepivital™, Manoliva™, Phyto-Age™, Timecode™; Survicode™; anti-photoaging active agents; agents for protecting the integrity of the dermoepidermal junction; active agents for increasing the synthesis of extracellular matrix components such as collagen, elastins, glycosaminoglycans; active agents which act favorably on chemical cell communication, such as cytokines, or physical cell communication, such as integrins; active agents which create a "heating" sensation on the skin, such as skin microcirculation activators (such as nicotinic acid derivatives) or products which create a feeling of "freshness" on the skin (such as menthol and derivatives); active agents for improving skin microcirculation, for example veinotonics; draining active agents; active agents for decongestive purposes, such as extracts of ginko biloba, of ivy, of horse chestnut, of bamboo, of ruscus, of butcher's broom, of Centalla asiatica, of fucus, of rosemary, of willow; agents for tanning or browning the skin, for instance dihydroxyacetone (DHA), erythrulose, mesotartaric aldehyde, glutaraldehyde, glyceraldehyde, alloxane, ninhydrin, plant extracts, for instance extracts of redwood of the genus Pterocarpus and of the genus Baphia, such as Pteropcarpus santalinus, Pterocarpus osun, Pterocarpus soyauxii, Pterocarpus *erinaceus, Pterocarpus indicus* or Baphia *nitida*, such as those described in European patent application EP 0 971 683; agents known for their action of facilitating and/or accelerating tanning and/or browning of the human skin and/or for their action of coloring the human skin, for example carotenoids (and more particularly beta-carotene and gamma-carotene), the product sold under the trade name "Carrot oil" (INCI name: *Daucus Carota, Helianthus annuus* Sunflower oil) by Provital, which contains carotenoids, vitamin E and vitamin K; tyrosine and/or the derivatives thereof, known for their effect on accelerating tanning of the human skin in combination with exposure to ultraviolet radiation, for instance the product sold under the trade name "SunTan Accelerator™" by Provital, which contains tyrosine and riboflavins (vitamin B), the tyrosine and tyrosinase complex sold under the trade name "Zymo Tan Complex" by Zymo Line, the product sold under the trade name MelanoBronze™ (INCI name: Acetyl Tyrosine, Monk's pepper extract (Vitex Agnus-castus)) by the company Mibelle, which contains acetyl tyrosine, the product sold under the trade name Unipertan VEG-24/242/2002 (INCI name: butylene glycol and Acetyl Tyrosine and hydrolyzed vegetable protein and Adenosine triphosphate) by the company Unipex, the product sold under the trade name "Try-Excell™" (INCI name: Oleoyl Tyrosine and Luffa *Cylindrica* (Seed Oil and Oleic acid) by the company Sederma, which contains extracts of marrow seed (or loofah oil), the product sold under the trade name Actibronze™ (INCI name: hydrolyzed wheat protein and acetyl tyrosine and copper gluconate) by the company Alban Muller, the product sold under the trade name Tyrostan™ (INCI name: potassium caproyl tyrosine) by the company Synerga, the product sold under the trade name Tyrosinol (INCI name: Sorbitan Isostearate, glyceryl oleate, caproyl Tyrosine) by Synerga, the product sold under the trade name Insta-Bronze™ (INCI name: Dihydroxyacetone and acetyl tyrosine and copper gluconate) sold by the company Alban Muller, the product sold under the trade name Tyrosilane (INCI name: methylsilanol and acetyl tyrosine) by the company Exymol; peptides known for their melanogenesis-activating effect, for example the product sold under the trade name Bronzing SF Peptide powder (INCI name: Dextran and Octapeptide-5) by Infinitec Activos, the product sold under the trade name Melitane (INCI name: Glycerin and Aqua and Dextran and Acetyl hexapeptide-1) comprising the acetyl hexapeptide-1 known for its alpha-MSH agonist action, the product sold under the trade name Melatimes Solutions™ (INCI name: Butylene glycol, Palmitoyl Tripeptide-40) by the company Lipotec, sugars and sugar derivatives, for example the product sold under the trade name Tanositol™ (INCI name: inositol) by the company Provital, the product sold under the trade name Thalitan™ (or Phycosaccharide™ AG) by the company CODIF international (INCI name: Aqua and hydrolyzed algin (*Laminaria Digitata*) and magnesium sulfate and manganese sulfate) containing an oligosaccharide of marine origin (guluronic acid and mannuronic acid chelated with magnesium and manganese ions), the product sold under the trade name Melactiva™ (INCI name: Maltodextrin, *Mucuna Pruriens* Seed extract) by the company Alban Muller, flavonoid-rich compounds, for instance the product sold under the trade name "Biotanning" (INCI name: Hydrolyzed citrus Aurantium *dulcis* fruit extract) by the company Silab and known to be rich in lemon flavonoids (of hesperidin type);

mineral fillers or pigments, such as titanium dioxide, brown iron oxides, yellow iron oxides, black iron oxides, or red iron oxides or else white or colored nacreous pigments such as titanium mica;

particles which provide a visual effect or which are intended for the encapsulating of active agents;

exfoliating particles;

optical brighteners;

insect repellents.

The oil-in-water emulsion (E) as defined above can be packaged in a bottle, in a device of pump "bottle" type, in the pressurized form in an aerosol device, in a device equipped with a perforated wall such as a grill, or in a device equipped with a roll-on applicator.

A subject of the invention is also the use of an oil-water-type emulsion for topical use (E) as defined above, for protecting human skin against the unesthetic effects of exposure to ultraviolet radiation from the sun, and more particularly against redness.

Finally, a subject of the invention is also an oil-in-water type emulsion (E) comprising, for 100% of its weight:

from 50% to 90% by weight, more particularly from 60% to 90% by weight and even more particularly from 70% to 90% by weight of a cosmetically acceptable aqueous phase (A);

from 10% to 50% by weight, more particularly from 10% to 40% by weight and even more particularly from 10% to 30% by weight of a fatty phase (G) comprising, for 100% of its weight:

from 10% to 50% by weight, more particularly from 15% to 40% by weight of a mixture ($M_1$) of saturated cyclic or acyclic, linear or branched hydrocarbons among which at least 95% by weight comprise from fifteen to nineteen carbon atoms;

from 0.5% to 15% by weight, more particularly from 1% to 10% by weight of at least one oil-in-water type surfactant;

from 5% to 30% by weight, more particularly from 15% to 30% by weight of at least one agent for protection against ultraviolet rays from the sun;

from 0% to 80% by weight, more particularly from 0% to 60% by weight of at least one oil and/or one wax, it being understood that such an oil and/or such a wax do not correspond to the definition of the mixture ($M_1$) it being understood that such an oil and/or such a wax do not correspond to the definition of the mixture ($M_1$), for use thereof in a therapeutic treatment method intended to prevent and/or treat human skin diseases linked to an exposure to ultraviolet radiation from the sun, more particularly burns, sunburn, erythema, skin cancers.

According to one particular aspect, said oil-in-water type emulsion (E) is free of shea butter.

DESCRIPTION OF THE PREFERRED EMBODIMENTS

The following examples illustrate the invention without, however, limiting it.

Preparation of Oil-In-Water Emulsions According to the Invention, Comprising a Mixture ($M_1$), and of Comparative Oil-In-Water Emulsions Four oil-in-water emulsions according to the invention, denoted ($E_1$) to ($E_4$), the weight proportions of the constituents of which are indicated in table 1, and six five comparative oil-in-water emulsions denoted ($F_1$) to ($F_5$), the weight proportions of the constituents of which are indicated in table 2 below, are prepared. The common preparation process for the oil-in-water emulsions according to the invention and for the comparative oil-in-water emulsions is as follows:

the oily mixture to be tested is poured into a beaker, at a temperature of 20° C., then where appropriate an optional second oil is gradually dispersed with mechanical stirring at 80 rpm;

the required amount of the Sepinov™MEMT 10 thickener is then added thereto with mechanical stirring at 80 rpm and at 20° C.;

the aqueous phase comprising the water and the Oramix™NS10 are prepared by mixing in a beaker, at a temperature of 20° C.;

the mixture then obtained is cooled with stirring of deflocculator type at 1500 revolutions per minute for 20 minutes, then emptied out so as to obtain the desired oil-in-water emulsion.

TABLE 1

| | Emulsion | | | |
| --- | --- | --- | --- | --- |
| | ($E_1$) | ($E_2$) | ($E_3$) | ($E_4$) |
| Fatty phase | | | | |
| Sepinov ™EMT 10[1] | 2% | 2% | 2% | 2% |
| Emosmar ™L19[2] | 15% | 0% | 12% | 3% |
| Emogreen ™L15[3] | 0% | 15% | 3% | 12% |
| Aqueous phase | | | | |
| Water | qs 100% | qs 100% | qs 100% | qs 100% |
| Oramix ™NS 10[4] | 0.3% | 0.3% | 0.3% | 0.3% |

[1](Sepinov ™EMT10): Thickener (INCI name: hydroxyethyl acrylate/acryloyldimethyltaurate acrylate copolymer),

[2](Emosmart ™L19): Mixture of saturated cyclic or acyclic, linear or branched hydrocarbons comprising, for 100% of its weight:
i) 13.20% by weight of linear alkanes comprising from 15 to 19 carbon atoms,
ii) 55.00% by weight of isoalkanes comprising from 15 to 19 carbon atoms,
iii) 31.80% of cycloalkanes comprising from 15 to 19 carbon atoms;

[3](Emogreen ™L15): Composition comprising, for 100% of its weight:
i) 3.7% of linear alkanes comprising from 15 to 19 carbon atoms,
ii) 96% of isoalkanes comprising from 15 to 19 carbon atoms,
iii) 0.3% of cycloalkanes comprising from 15 to 19 carbon atoms;

[4](Oramix ™S10): solubilizing foaming agent (INCI name: capryloyl/capryl glucoside).

TABLE 2

| | Emulsion | | | | |
| --- | --- | --- | --- | --- | --- |
| | ($F_1$) | ($F_2$) | ($F_3$) | ($F_4$) | ($F_5$) |
| Fatty phase | | | | | |
| Sepinov ™EMT 10 | 2% | 2% | 2% | 2% | 2% |
| Isohexadecane | 15% | 0% | 0% | 0% | 0% |
| DC 345[5] | 0% | 15% | 0% | 0% | 0% |

TABLE 2-continued

| | Emulsion | | | | |
|---|---|---|---|---|---|
| | ($F_1$) | ($F_2$) | ($F_3$) | ($F_4$) | ($F_5$) |
| DC 245[6] | 0% | 0% | 15% | 0% | 0% |
| Emosmart ™L15[7] | 0% | 0% | 0% | 15% | 0% |
| Emosmart ™V21[8] | 0% | 0% | 0% | 0% | 15% |
| Aqueous phase | | | | | |
| Water | qs 100% | qs 100% | qs 100% | qs 100% | qs 100% |
| Oramix ™NS10 | 0.3% | 0.3% | 0.3% | 0.3% | 0.3% |

[5](DC 345): Emollient used in cosmetics for the sensory properties that it provides and more particularly the ease of spreading that it confers on the emulsion containing it (INCI name: cyclopentasiloxane & cyclohexasiloxane);
[6](DC 245): Emollient used in cosmetics for the sensory properties that it provides and more particularly the ease of spreading that it confers on the emulsion containing it (INCI name: cyclopentasiloxane);
[7](Emosmart ™L15): Mixture comprising, for 100% of its weight:
i) 9.26% by weight of linear alkanes comprising from 13 to 15 carbon atoms,
ii) 39.06% by weight of isoalkanes comprising from 13 to 15 carbon atoms,
iii) 51.68% of cycloalkanes comprising from 13 to 15 carbon atoms;
[8](Emosmart ™V21): Mixture comprising, for 100% of its weight:
i) 15.99% by weight of linear alkanes comprising from 18 to 21 carbon atoms,
ii) 59.90% by weight of isoalkanes comprising from 18 to 21 carbon atoms,
iii) 24.11% of cycloalkanes comprising from 18 to 21 carbon atoms.

Evaluation of the Spreading Properties of an Oil-In-Water Emulsion According to the Invention and of Comparative Oil-In-Water Emulsions Principle of the Method The spreading properties of an oil-in-water emulsion are evaluated by the variation in a mean of measurements of the value of the coefficient of friction of said emulsion, carried out using a rheometer of type DHR2 (from the company Texas Instruments), for various spreading speeds.

Principle of the Measurement

It involves characterizing each emulsion tested for a mean value of 3 measured values of the coefficient of friction, in normal force, for a velocity of 1 radian·$s^{-1}$ and of 4 radian·$s^{-1}$, then calculating the percentage change for the mean obtained at each of the two speeds.

Material and Equipment

The measurements are carried out by means of a DHR2 rheometer (TA Instruments) equipped with the "Tribo Ring on Plate" accessory on which is placed a surface of plexiglass onto which the emulsion to be tested is deposited.

Procedure

An amount of the emulsion to be tested is deposited, using a calibrated spreader, such that it forms a thickness of 90 micrometers on the plate.

After deposition of the sample, its calibrated thickness is brought into contact with the "Tribo Ring on Plate" geometry, and a normal force of 2 N and a fixed velocity gradient that can be adjusted to a value of between 0.01 and 15 radian·$s^{-1}$ are applied.

The maximum normal force of friction to which the Peltier plate is subjected during the rotation of the geometry is measured.

Expression of the Results

For each emulsion tested, and for each performed measurement of the value of the maximum normal force of friction, the coefficient of friction (Cf) is calculated as follows:

Cf=(value maximum normal force of friction)/(value normal force applied)

For each emulsion tested, the values obtained during 3 statistically significant measurements, for a fixed velocity at 1 radian·$s^{-1}$ and for a fixed velocity at 4 radian·$s^{-1}$, are taken into consideration, and for each of the emulsions tested, the mean value of the values of the coefficients of friction thus experimentally obtained, denoted $Cf_m$ for a fixed velocity at 1 radian·$s^{-1}$ and $Cf_{m4}$ for a fixed velocity at 4 radian·$s^{-1}$, are calculated.

The variation (denoted ΔCf) between the mean value of the coefficient of friction obtained for a velocity of 1 radian·$s^{-1}$ and the mean value of the coefficient of friction obtained for a fixed velocity at 4 radian·$s^{-1}$ is then calculated as follows:

$$\Delta_{cf} = (Cf_{m1} - Cf_{m4})/(Cf_{m1}) \times 100$$

Results

The results obtained are recorded in table 3 hereinafter.

TABLE 3

| | Emulsion | | | |
|---|---|---|---|---|
| | ($E_1$) | ($F_1$) | ($F_2$) | ($F_3$) |
| $\Delta_{Cf}$ | −6.8% | +18.2% | +17.5% | +14.5% |

Analysis of the Results

The results recorded in table 3 clearly reveal that the variation in the means of the coefficients of friction, between spreading at a velocity of 1 radian·$s^{-1}$ and a velocity of 4 radian·$s^{-1}$, for the emulsion ($E_1$) according to the invention is less than a value of 10% (−6.8%), whereas the comparative emulsions ($F_2$) and ($F_3$), comprising silicone oils known to confer improved spreading on the emulsions that contain them, show a variation in the coefficient of friction of greater than 15% between spreading at a velocity of 1 radian·$s^{-1}$ and a velocity of 4 radian·$s^{-1}$.

These results thus show an improvement in the ease of spreading of the emulsions according to the invention compared with emulsions comprising emollients known to impart an ease of spreading on the emulsions containing them.

The variation in the means of the coefficients of friction, between spreading at a velocity of 1 radian·$s^{-1}$ and a velocity of 4 radian·$s^{-1}$ for the comparative emulsion ($F_1$), comprising isohexadecane, that is to say an isoparaffin comprising 16 carbon atoms, shows a value of 18.2%, that is to say less performance and less ease of spreading for the emulsions comprising this isoparaffin comprising 16 carbon atoms, than for the emulsions according to the invention.

Finally, the negative variation of the mean of the coefficients of friction, between a velocity of 1 radian·$s^{-1}$ and a velocity of 4 radian·$s^{-1}$, shows an additional technical benefit, namely the obtaining of a lower mean value of the coefficient of friction for a low velocity, that is to say a possibility of spreading the emulsion according to the invention on the skin more easily.

Evaluation of the sensory properties of oil-in-water emulsions according to the invention and of comparative oil-in-water emulsions Principle of the Method 13 duly trained and authorized panellists evaluated the criteria of "sensation of richness", of "shininess of the skin" and of "shininess of the emulsion" of oil-in-water emulsions according to the invention and of comparative oil-in-water emulsions, by taking as reference base an emulsion known by those skilled in the art to constitute an emulsion for which the richness criterion is recognized by all of the panellists, and also a comparison reference to be surpassed in order to realize the stated technical problem.

Procedure

The procedure carried out comprises 5 steps which are the following:

Step 1: control and evaluation of the appearance and the odor of the oil-in-water emulsion tested, Step 2: take-up in the hand: evaluation of the ease of taking hold, and observation of a possible runny appearance, Step 3: spreading of the tested emulsion on the skin by circular application to the surface of the skin, at one and the same speed for 10 circular movements, and collection of the sensations perceived at the end of the $10^{th}$ circular movement, Step 4: continuation of the spreading of the tested emulsion on the skin, still by application of the same circular movement until the absence of emulsion film is observed, and gathering of the perceived sensations, Step 5: gathering of the perceived sensations after 1 minute after the end of the spreading.

This procedure is carried out at a temperature of 20° C.

Expression of the Results:

For each emulsion tested, and for each sensory criterion evaluated, each panellist indicates whether said emulsion tested provides an improved sensation compared with the reference emulsion. All of the evaluations are collected and the data are statistically processed so as to determine the significant nature of any difference, improvement or degradation, between the sensation perceived for the emulsion tested and the reference emulsion.

Results

"Sensation of Richness" Criterion

Reference emulsion: emulsion ($F_4$).

The emulsions according to the invention ($E_1$) and ($E_3$), and also the comparative emulsions ($F_2$) and ($F_5$) are evaluated according to the protocol defined above, and the results obtained are recorded in table 4 below. The improvement in the sensation of richness compared with ($F_4$) is denoted "> ($F_4$)" and the deterioration of the sensation of richness compared with ($F_4$) is denoted "< ($F_4$)" at each moment of the spreading process.

TABLE 4

| | Emulsion | | | |
|---|---|---|---|---|
| | ($E_1$) | ($E_3$) | ($F_2$) | ($F_5$) |
| Step 1: Visual evaluation | >($F_4$) | >($F_4$) | <($F_4$) | <($F_4$) |
| Step 2: Evaluation of taking hold | >($F_4$) | >($F_4$) | <($F_4$) | <($F_4$) |
| Step 3: Evaluation after the first 10 circular movements | >($F_4$) | >($F_4$) | <($F_4$) | <($F_4$) |
| Step 4: Evaluation after penetration | >($F_4$) | >($F_4$) | <($F_4$) | <($F_4$) |
| Step 5: Evaluation 1 minute after end of spreading | >($F_4$) | >($F_4$) | <($F_4$) | <($F_4$) |

"Shininess of the Skin" Criterion

Reference emulsion: emulsion ($F_4$).

The emulsions according to the invention ($E_1$) and ($E_3$), and also the comparative emulsions ($F_2$) and ($F_5$) are evaluated according to the protocol defined above, and the results obtained are recorded in table 5 below. The increase in the shininess of the skin compared with ($F_4$) is denoted "> ($F_4$)" and its decrease is denoted "< ($F_4$)".

TABLE 5

| | Emulsion | | | |
|---|---|---|---|---|
| | ($E_1$) | ($E_3$) | ($F_2$) | ($F_5$) |
| Step 5: Evaluation 1 minute after end of spreading | <($F_4$) | <($F_4$) | >($F_4$) | >($F_4$) |

"Shininess of the Emulsion" Criterion

The emulsions according to the invention ($E_1$) and ($E_3$), and also the comparative emulsions ($F_2$) and ($F_5$) are evaluated according to the protocol defined above, and the results obtained are recorded in table 5 below. The increase in the shininess of the emulsion compared with ($F_4$) is denoted "> ($F_4$)" and its decrease is denoted "< ($F_4$)".

TABLE 6

| | Emulsion | | | |
|---|---|---|---|---|
| | ($E_1$) | ($E_3$) | ($F_2$) | ($F_5$) |
| Step 1: Visual evaluation | >($F_4$) | >($F_4$) | <($F_4$) | <($F_4$) |

Analysis of the Results

The results obtained show the improvement in the sensory and esthetic properties by virtue of the method according to the invention.

Illustrative Formulae

| Ingredients | % (by weight) |
|---|---|
| Antisun emulsion | |
| Polyacrylate Crosspolymer-6 (SEPIMAX ™ ZEN) | 0.90% |
| Glycerol | 1.50% |
| Water | qs 100% |
| Easynov ™ | 3.00% |
| EMOGREEN ™L15 | 12.00% |
| Sepicide ™HB | 1.00% |
| Fragrance | 0.30% |
| Titanium Dioxide And Alumina And Stearic Acid | 10.00% |
| High UV protection antisun fluid | |
| Montanov ™ 82 | 2.00% |
| C12-15 Alkyl Benzoate | 17.00% |
| Octocrylene | 6.00% |
| Ethylhexyl Methoxycinnamate | 6.00% |
| Bis-Ethylhexylphenol Methoxyphenyl triazine | 3.00% |
| Emogreen ™L19 | 3.00% |
| Tocopherol | 0.05% |
| Polyacrylate Crosspolymer-6 (SEPIMAX ™ ZEN) | 0.25% |
| Cyclopentasiloxane | 5.00% |
| Titanium Dioxide And Isohexadecane And Triethylhexanoin And Aluminum Stearate And Alumina And Polyhydroxystearic Acid | 5.40% |
| Water | qs 100% |
| Methylene Bis-Benzotriazolyl Tetramethylbutylphenol | 10.00% |
| Citric Acid | qs pH 5.5 |
| Aquaxyl ™ | 3.00% |
| Phenoxyethanol Ethylhexylglycerin | 1.00% |
| Fragrance | 0.20% |
| High UV protection antisun fluid | |
| Montanov ™ 82 | 2.00% |
| C12-15 Alkyl Benzoate | 17.00% |
| Octocrylene | 6.00% |
| Ethylhexyl Methoxycinnamate | 6.00% |
| 2-Ethylhexyl dimethoxybenzylidene dioxoimidazolidine propionate | 3.00% |
| Emogreen ™L15 | 3.00% |
| Tocopherol | 0.05% |
| Polyacrylate Crosspolymer-6 (SEPIMAX ™ ZEN) | 0.25% |

-continued

| Ingredients | % (by weight) |
|---|---|
| Cyclopentasiloxane | 5.00% |
| Titanium Dioxide And Isohexadecane And Triethylhexanoin And Aluminum Stearate And Alumina And Polyhydroxystearic Acid | 5.40% |
| Water | qs 100% |
| Methylene Bis-Benzotriazolyl Tetramethylbutylphenol | 10.00% |
| Citric Acid | qs pH 5.5 |
| Aquaxyl ™ | 3.00% |
| Phenoxyethanol Ethylhexylglycerin | 1.00% |
| Fragrance | 0.20% |
| Hair balm | |
| Water | qs 100% |
| Glycerin | 1.50% |
| Propanediol | 1.50% |
| Polyacrylate Crosspolymer-6 (SEPIMAX ™ ZEN) | 1.50% |
| Cera Alba | 2.00% |
| Copernica Cerifera | 1.00% |
| Butyrospermum parkii | 2.00% |
| Prunus amygdalus dulcis | 4.00% |
| Simmondsia chinensis seed oil | 6.00% |
| Emogreen ™L15 | 3.00% |
| Montanov ™ 202 | 2.50% |
| Cetearyl Alcohol | 3.00% |
| Aquaxyl ™ | 3.00% |
| Tocopherol & Helianthus annuus seed oil | 0.10% |
| Benzyl alcohol & Dehydroacetic acid | 0.70% |
| Citrus aurantium peel oil | 0.20% |
| Sodium chloride | 1.00% |
| Sodium Hydroxide | qs pH 5.5 |

SEPIMAX ™ Zen (Polyacrylate Crosspolymer-6) is a thickening and stabilizing anionic polymer sold by the company SEPPIC.
Easynov ™ (Octyldodecanol & Octydodecyl Xyloside & PEG-30 Dipolyhydroxystearate) is a water-in-oil type emulsifier sold by the company SEPPIC.
Solagum ™ AX (Acacia Senegal Gum and Xanthan Gum) is a thickening and stabilizing polymer of natural origin, sold by the company SEPPIC.
Montanov ™ 82 (Cetearyl Alcohol & Cocoglucoside) is an oil-in-water type emulsifier sold by the company SEPPIC.
Aquaxyl ™ (Xylitylglucoside and Anhydroxylitol and Xylitol) is a moisturizing active agent sold by the company SEPPIC.
Sepicide ™ HB (Phenoxyethanol & Methylparaben & Ethylparaben & Propylparaben & Butylparaben) is a preserving composition sold by the company SEPPIC. Citrus Waterfall fragrance concentrate is sold by the company Mane.
Montanov ™ 202 (Arachidyl Alcohol (and) Behenyl Alcohol (and) Arachidyl Glucoside) is an oil- in-water type emulsifier sold by the company SEPPIC.

The invention claimed is:

1. A method for improving the spreading properties of an oil-in-water emulsion for topical use,
wherein said oil-in-water emulsion comprises for 100% of its weight:
from 95% to 50% wt % of a cosmetically acceptable aqueous phase;
from 5% to 50% wt % of a fatty phase, said fatty phase comprising, for 100% of the weight of said fatty phase, from 1% to 12% wt % of at least one oil-in-water surfactant and from 88% to 99% wt % of at least one oil and/or one wax,
the method comprising adding into said oil-in-water emulsion from 1% to 25% wt % of said oil-in-water emulsion of a mixture of saturated hydrocarbons that are cyclic or acyclic, linear or branched,
wherein said mixture of saturated hydrocarbons comprises, for 100% of its weight,
either:
80-100 wt % of branched alkanes,
0-15 wt % of linear alkanes, and
0-5 wt % of cycloalkanes, and
wherein from 95% by weight to 100% by weight of said cyclic or acyclic, linear or branched saturated hydrocarbons comprise from fifteen to nineteen carbon atoms and up to 5% by weight of said cyclic or acyclic, linear or saturated branched hydrocarbons comprise less than fifteen or more than nineteen carbon atoms,
or:
40-100 wt % of branched alkanes,
0-20 wt % of linear alkanes, and
0-40 by weight of cycloalkanes and
wherein 100% by weight of said cyclic or acyclic, linear or branched saturated hydrocarbons comprise from fifteen to nineteen carbon atoms,
wherein said oil-in-water emulsion is free of shea butter,
wherein said oil-in-water emulsion is free of silicone oil and silicone derivatives, and
wherein said oil-in-water emulsion further comprises at least one terpolymer selected from the group consisting of
terpolymers of acrylic or methacrylic acid in combination with 2-methyl-[(1-oxo-2-propenyl)aminol-1-propanesulfonic acid (AMPS) and N,N-dimethylacrylamide,
terpolymers of acrylic or methacrylic acid in combination with AMPS, and acrylamide, and
linear, branched, or crosslinked terpolymers with one monomer having a free partially salified or totally salified strong acid function, in combination with one neutral monomer, and one monomer of formula:
$CH_2=C(R'_3)-C(=O)-[CH_2-CH_2-O]_n-R'_4$
wherein $R'_3$ represents a hydrogen atom or a methyl radical, $R'_4$ represents a linear or branched alkyl radical comprising from eight to thirty carbon atoms, and n represents a number that is greater or equal to one and less or equal to 50.

2. The method as defined in claim 1, wherein said mixture of saturated hydrocarbons comprises, for 100% of its weight:
50-100 wt % of branched alkanes,
0-15 wt % of linear alkanes, and
0-35 wt % of cycloalkanes, and
wherein 100% by weight of said cyclic or acyclic, linear or branched saturated hydrocarbons comprise from fifteen to nineteen carbon atoms.

3. The method as defined in claim 1, wherein said mixture of saturated hydrocarbons comprises, for 100% of its weight:
90-100 wt % of branched alkanes,
0-10 wt % of linear alkanes, and
0-1 wt % of cycloalkanes, and
wherein from 95% by weight to 100% by weight of said cyclic or acyclic, linear or branched saturated hydrocarbons comprise from fifteen to nineteen carbon atoms and up to 5% by weight of said cyclic or acyclic, linear or branched saturated hydrocarbons comprise less than fifteen or more than nineteen carbon atoms.

4. The method as defined in claim 2, wherein said mixture of saturated hydrocarbons comprises, for 100% of its weight:
13.2 wt % of linear alkanes,
55.0 wt % of isoalkanes, and
31.8 wt % of cycloalkanes.

5. The method as defined in claim 3, wherein said mixture of saturated hydrocarbons comprises, for 100% of its weight:
3.7 wt % of linear alkanes comprising from fifteen to nineteen carbon atoms,
96 wt % of isoalkanes comprising from fifteen to nineteen carbon atoms, and
0.3 wt % of cycloalkanes comprising from fifteen to nineteen carbon atoms.

6. The method according to claim 1, wherein said oil-in-water emulsion comprises, for 100% of its weight:

from 90% to 70% wt % of a cosmetically acceptable aqueous phase;
from 10% to 30% wt % of a fatty phase, said fatty phase comprising, for 100% of the weight of said fatty phase, from 2% to 8% wt % of at least one oil-in-water surfactant and from 92% to 98% wt % of at least one oil and/or one wax.

7. The method as defined in claim 6, wherein said mixture of saturated hydrocarbons comprises, for 100% of its weight:
   a weight proportion of branched alkanes of greater than or equal to 50% and less than or equal to 100%,
   a weight proportion of linear alkanes of greater than or equal to 0% and less than or equal to 15%,
   a weight proportion of cycloalkanes of greater than or equal to 0% and less than or equal to 35%,
   and
   wherein 100% by weight of said cyclic or acyclic, linear or branched saturated hydrocarbons comprise from fifteen to nineteen carbon atoms.

8. The method as defined in claim 6, wherein said mixture of saturated hydrocarbons comprises, for 100% of its weight:
   a weight proportion of branched alkanes of greater than or equal to 90% and less than or equal to 100%,
   a weight proportion of linear alkanes of greater than or equal to 0% and less than or equal to 10%,
   a weight proportion of cycloalkanes of greater than or equal to 0% and less than or equal to 1%,
   and
   wherein from 95% by weight to 100% by weight of said cyclic or acyclic, linear or branched saturated hydrocarbons comprise from fifteen to nineteen carbon atoms and up to 5% by weight of said cyclic or acyclic, linear or saturated branched hydrocarbons comprise less than fifteen or more than nineteen carbon atoms.

9. The method as defined in claim 7, wherein said mixture of saturated hydrocarbons comprises, for 100% of its weight:
   13.2 wt % of linear alkanes,
   55.0 wt % of isoalkanes, and
   31.8 wt % of cycloalkanes.

10. The method as defined in claim 8, wherein said mixture of saturated hydrocarbons comprises, for 100% of its weight:
   3.7 wt % of linear alkanes comprising from fifteen to nineteen carbon atoms,
   96 wt % of isoalkanes comprising from fifteen to nineteen carbon atoms, and
   0.3 wt % of cycloalkanes comprising from fifteen to nineteen carbon atoms.

* * * * *